US008865157B2

(12) United States Patent
Upton et al.

(10) Patent No.: US 8,865,157 B2
(45) Date of Patent: Oct. 21, 2014

(54) ANTIMICROBIAL PEPTIDES

(75) Inventors: Mathew Upton, Manchester (GB); Stephanie Sandiford, Manchester (GB)

(73) Assignee: The University of Manchester (GB)

( * ) Notice: Subject to any disclaimer, the term of this patent is extended or adjusted under 35 U.S.C. 154(b) by 0 days.

(21) Appl. No.: 13/516,534

(22) PCT Filed: Dec. 16, 2010

(86) PCT No.: PCT/GB2010/052106
§ 371 (c)(1),
(2), (4) Date: Aug. 17, 2012

(87) PCT Pub. No.: WO2011/073663
PCT Pub. Date: Jun. 23, 2011

(65) Prior Publication Data
US 2012/0308638 A1  Dec. 6, 2012

(30) Foreign Application Priority Data

Dec. 17, 2009 (GB) .................................. 0921995.7

(51) Int. Cl.
*A61K 38/44* (2006.01)
(52) U.S. Cl.
USPC ....................................................... 424/93.44
(58) Field of Classification Search
None
See application file for complete search history.

(56) References Cited

FOREIGN PATENT DOCUMENTS

WO    WO 9014098 A1 * 11/1990

OTHER PUBLICATIONS

Iwatani et al. "Characterization and Structure Analysis of a Novel Bacteriocin, Lacticin Z, Produced by *Lactococcus lactis*QU 14", *Biosci. Biotechnol. Biochem.* 71:1984-1992 (2007).

Netz et al. "Biochemical Characterisation and Genetic Analysis of Aureocin A53, a New, Atypical Baceriocin from *Staphylococcus aureus*",*J. Mol. Biol.* 319:745-756 (2002).
Fujita et al. "Structural Analysis and Characterization of Lacticin Q, a Novel Bacteriocin Belonging to a New Family of Unmodified Bacteriocins of Gram-Positive Bacteria", *Applied and Environmental Microbiology*73(9):2871-2877 (2007).
Database UniProt [Online] "Subname: Full=Acetoacetyl-CoA synthase" http://ibis.internal.epo.ord/IBIS/exam/dbfetch.jsp?id=UNIPROT:C6VXU1 (2011).
Notification Concerning Transmittal of Copy of International Preliminary Report on Patentability corresponding to PCT Application No. PCT/GB2010/052106 mailed Jun. 28, 2012.
Iwatani et al. "Characterization and Structure Analysis of a Novel Bacteriocin, Lacticin Z, Produced by *Lactococcus lactis* Qu 14", *Biosci. Biotechnol. Biochem.* 71(*):1984-1992.
Netz et al. "Biochemical Characterisation and Genetic Analysis of Aureocin A53, a New, Atypical Baceriocin from *Staphylococcus aureus*", *J. Mol. Biol.* 319:745-756 (2002).
Fujita et al. "Structural Analysis and Characterization of Lacticin Q, a Novel Bacteriocin Belonging to a New Family of Unmodified Bacteriocins of Gram-Positive Bacteria", *Applied and Environmental Microbiology* 73(9):2871-2877 (2007).
Database UniProt [Online] "Subname: Full=Acetoacetyl-CoA synthase" *http://ibis.internal.epo.org/IBIS/exam/dbfetch.jsp?id=UNIPROT:C6VXU1* (2011).
Notification of Transmittal of the International Search Report and the Written Opinion of the International Searching Authority, or the Declaration corresponding to PCT Application No. PCT/GB2010/052106 mailed May 9, 2011.

* cited by examiner

*Primary Examiner* — Susan Tran
(74) *Attorney, Agent, or Firm* — Myers Bigel Sibley & Sajovec, P.A.

(57) ABSTRACT

The present invention provides novel therapeutic antimicrobial peptides that are bactericides and have an inhibitory effect on biofilms produced by biofilm-forming bacteria and especially biofilm-forming staphyloccocal bacteria. The invention includes the nucleic acids encoding the polypeptides, methods of treating bacterial infections, medical devices or implants or prosthetics impregnated with, covered or coated in the polypeptides, and means of delivery of the peptide to the oral cavity.

17 Claims, 8 Drawing Sheets

SEQ ID NO:2

```
      Met  Ala  Ala  Phe  Met  Lys  Leu  Ile  Gln  Phe  Leu  Ala   12
  1   ATG  GCA  GCA  TTT  ATG  AAG  TTA  ATT  CAG  TTC  TTA  GCA
      Thr  Lys  Gly  Gln  Lys  Tyr  Val  Ser  Leu  Ala  Trp  Lys   24
 37   ACT  AAA  GGT  CAA  AAG  TAT  GTT  TCA  CTT  GCA  TGG  AAA
      His  Lys  Gly  Thr  Ile  Leu  Lys  Trp  Ile  Asn  Ala  Gly   36
 73   CAT  AAA  GGT  ACT  ATT  TTA  AAA  TGG  ATT  AAC  GCC  GGT
      Gln  Ser  Phe  Glu  Trp  Ile  Tyr  Lys  Gln  Ile  Lys  Lys   48
109   CAA  AGT  TTT  GAA  TGG  ATT  TAT  AAA  CAA  ATC  AAA  AAA
      Leu  Trp  Ala  Stop                                          51
145   TTA  TGG  GCA  TAA
```

FIG. 3

```
                  10         20         30         40         50
          ....|....|....|....|....|....|....|....|....|....|....|...
peptideNl01  MAAFMKLIQFLATKGQKYVSLAWKHKGTILKWINAGQSFEWIYKQIKKLWA--
Lacticin Q   MAGFLKVVQLLAKYGSKAVQWAWANKGKILDWLNAGQAIDWVVSKIKQILGIK
Lacticin Z   MAGFLKVVQILAKYGSKAVQWAWANKGKILDWINAGQAIDWVVEKIKQILGIK
               ** *  *  ** *  * **  ** **  ****  *       **
```

FIG. 4

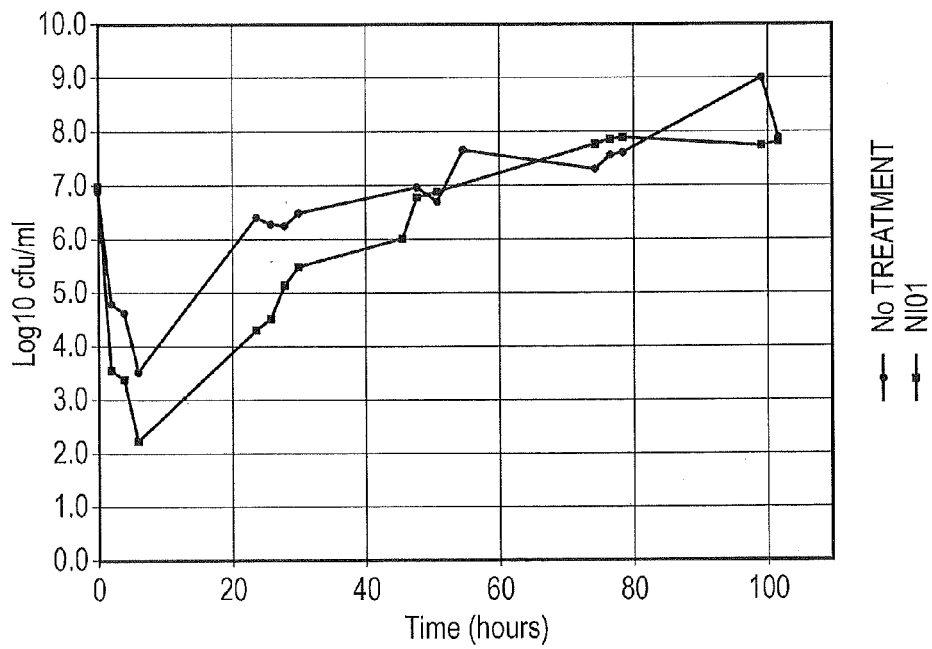

FIG. 5

SEQUENCE LISTING

<160> NUMBER OF SEQ ID NOS: 5

<210> SEQ ID NO 1
<211> LENGTH: 15
<212> TYPE: PRT
<213> ORGANISM: Unknown
<220> FEATURE:
<223> OTHER INFORMATION: antimicrobial polypeptide

<400> SEQUENCE: 1

Gln Ser Phe Glu Trp Ile Tyr Lys Gln Ile Lys Lys Leu Trp Ala
1               5                   10                  15

<210> SEQ ID NO 2
<211> LENGTH: 156
<212> TYPE: DNA
<213> ORGANISM: Unknown
<220> FEATURE:
<223> OTHER INFORMATION: DNA sequenec encoding structural gene of NOI01

<400> SEQUENCE: 2
atggcagcat ttatgaagtt aattcagttc ttagcaacta aaggtcaaaa gtatgtttca      60
cttgcatgga acataaagg tactatttta aaatggatta acgccggtca aagttttgaa     120
tggatttata aacaaatcaa aaaattatgg gcataa                              156

<210> SEQ ID NO 3
<211> LENGTH: 51
<212> TYPE: PRT
<213> ORGANISM: Unknown
<220> FEATURE:
<223> OTHER INFORMATION: NOI01 polypeptide

<400> SEQUENCE: 3

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50

<210> SEQ ID NO 4
<211> LENGTH: 53
<212> TYPE: PRT
<213> ORGANISM: Lactococcus lactis QU 14

<400> SEQUENCE: 4

Met Ala Gly Phe Leu Lys Val Val Gln Ile Leu Ala Lys Tyr Gly Ser
1               5                   10                  15

-continued

```
Lys Ala Val Gln Trp Ala Trp Ala Asn Lys Gly Lys Ile Leu Asp Trp
            20                  25                  30

Ile Asn Ala Gly Gln Ala Ile Asp Trp Val Val Glu Lys Ile Lys Gln
        35                  40                  45

Ile Leu Gly Ile Lys
    50

<210> SEQ ID NO 5
<211> LENGTH: 53
<212> TYPE: PRT
<213> ORGANISM: Lactococcus lactis QU 5

<400> SEQUENCE: 5

Met Ala Gly Phe Leu Lys Val Val Gln Leu Leu Ala Lys Tyr Gly Ser
1               5                   10                  15

Lys Ala Val Gln Trp Ala Trp Ala Asn Lys Gly Lys Ile Leu Asp Trp
            20                  25                  30

Leu Asn Ala Gly Gln Ala Ile Asp Trp Val Val Ser Lys Ile Lys Gln
        35                  40                  45

Ile Leu Gly Ile Lys
    50
```

ANTIMICROBIAL PEPTIDES

CROSS REFERENCE TO RELATED APPLICATIONS

The present application is a 35 U.S.C. §371 national phase application of PCT International Application No. PCT/GB2010/052106, having an international filing date of, Dec. 16, 2010, claiming priority to British Patent Application No. 0921995.7 filed Dec. 17, 2009. The disclosures of each application are incorporated herein by reference in their entireties. The above PCT International Application was published in the English language and has International Publication No. WO 2011/073663 A1.

STATEMENT REGARDING ELECTRONIC FILING OF A SEQUENCE LISTING

A Sequence Listing in ASCII text format, submitted under 37 C.F.R. §1.821, entitled 9052-317_ST25.txt, 2,492 bytes in size, generated on Jun. 14, 2012 and filed via EFS-Web, is provided in lieu of a paper copy. This Sequence Listing is hereby incorporated by reference into the specification for its disclosures.

The present invention relates to novel antimicrobial peptides and nucleic acids encoding them, the polypeptides having an inhibitory effect on biofilms produced by biofilm-forming bacteria and especially biofilm-forming Staphloccocus bacteria. The invention includes inter alia methods of treating bacterial infections and preventing the spread of the infections or contamination by the infection. The peptides of the present invention are of particular use as therapeutics to treat Staphlococcal infections and of use in impregnation of and covering or coating medical devices or implants or prosthetics.

BACKGROUND

Bacteria in the genus Staphylococcus are pathogenic to man and other mammals and are traditionally divided into two groups on the basis of their ability to clot blood plasma (the coagulase reaction). The coagulase-positive staphylococci constitute the most pathogenic species S aureus and whilst coagulase is a marker for S aureus there is no direct evidence that it is a virulence factor. There are over 30 species of coagulase-negative staphylococcus(CNS) and these are common commensals of skin, although some species can cause infections. S. saprophyticus, is a CNS species that is part of the normal vaginal flora and is predominantly implicated in genitourinary tract infections in sexually-active young women. In recent years, several other Staphylococcus species have been implicated in human infections, notably S. lugdunensis, S. schleiferi, and S. caprae. However, the most prevalent CNS species is S. epidermidis which is a commensal of the skin and can also be found in mucous membranes. Little is known about how S. epidermidis causes disease in humans but colonisation of medical devices has led to an acknowledgement of the significance of CNS in infection. A characteristic of many strains of this microbe is the production of a capsule or slime resulting in the formation of a biofilm. In a biofilm, S. epidermidis is protected against attacks from the immune system and against antibiotic treatment, making S. epidermidis infections difficult to stop. Although S. epidermidis is usually non-pathogenic, these bacteria are responsible for a growing number of infections among hospital patients whose immune systems are weakened or compromised and in immuno-competent individuals with indwelling medical devices. Such infections often occur because the bacterium is carried from the surface of the skin to deeper tissues and the blood stream by insertion of venous catheters or peritoneal dialysis catheters. These infections can be both nosocomial or community acquired, but they are more of a threat to hospital patients. This is in part due to hospitals harboring more virulent strains of the organism and the continuous use of antibiotics and disinfectants. S. epidermidis is a major concern for individuals with catheters or other surgical implants because it is known to cause biofilms that grow on such devices, especially on intravenous catheters and on medical prostheses. Infection can also occur in dialysis patients or anyone with an implanted medical device that may have been contaminated. S. epidermidis has also been associated with endocarditis and occurs most frequently in patients with defective heart valves. It is also responsible for many cases of late-onset sepsis in newborns.

As S. epidermidis is part of the human normal flora, it has developed resistance to many common antibiotics such as methicillin, novobiocin, clindamycin, and benzyl penicillin. Most infections require treatment with antibiotics that are effective, such as vancomycin (although cases of S. epidermidis resistant to vancomycin are now appearing), rifampin, linezolid, quinupristin/dalfopristinand and newer quinolones such as gatifloxacin and moxifloxacin. In addition, effective treatment usually requires removal of any implanted medical device that is infected with S. epidermidis, such as indwelling venous catheters, and prosthetic (artificial) heart valves and joints. The pathogenicity of CNS species is related to their ability to form biofilms especially on plastic medical devices and is a major virulence factor.

To survive during colonization or infection of the human body, microorganisms must circumvent mechanisms of innate host defense. Antimicrobial peptides (also known as natural antibiotics) represent a key component of innate host defense, especially in phagocytes and on epithelial surfaces. Antimicrobial peptides derived from humans and other higher animals are potent, broad-spectrum antibiotics and those of bacterial origin tend to have a more focused spectrum of activity. Both types of peptide demonstrate potential as alternative novel therapeutic agents. The interaction of the peptides with susceptible cells is thought to occur via ionic interactions and results in cell death by destabilization of the membranes and/or pore formation. Although there have been several reports in the literature regarding the use of antimicrobial peptides to treat S. epidermidis infections no suitable therapeutic has emerged.

The increasing resistance of CNS species to many synthetic antibiotics emphasizes the urgent need for new and more effective antimicrobial agents. There is a need for new and effective preventive and therapeutic treatments for CNS species infections.

BRIEF SUMMARY OF THE DISCLOSURE

According to a first aspect of the invention there is provided an isolated or recombinant polypeptide comprising a C terminal polypeptide sequence QSFEWIYKQIKKLWA [SEQ ID NO:1] or having at least 90% identity thereto, wherein the isolated or recombinant polypeptide is bactericidal.

According to a further aspect of the invention there is provided an isolated or recombinant nucleic acid sequence comprising a sequence encoding a polypeptide comprising a C terminal polypeptide sequence QSFEWIYKQIKKLWA [SEQ ID NO:1] or having at least 90% identity thereto, wherein the encoded polypeptide is bactericidal.

According to a yet further aspect of the invention there is provided an isolated or recombinant polypeptide comprising the sequence as depicted in SEQ ID NO:3 or variant thereof, said variant being:
a) a polypeptide comprising a sequence has at least 55% sequence identity with SEQ ID NO:3; or
b) a polypeptide comprising the sequence of SEQ ID NO:1 except for at least the first N-terminal amino acid and at most the first 37 N-terminal amino acids of SEQ ID NO:3; or
c) a polypeptide comprising one or more point mutations or amino acid substitutions or deletions in the sequence of SEQ ID NO:3; or
d) a polypeptide comprising in addition to the sequence of SEQ ID NO: 3 sequences representing marker moieties, tags or other functional polypeptide sequences; or
e) a polypeptide comprising one or more additional amino acid residues inserted into the amino acid sequence according to SEQ ID NO:3; or
f) a polypeptide comprising a polypeptide sequence representing any combination of variants a), b), c), d) and e).

According to a yet further aspect of the invention there is provided a nucleic acid sequence as depicted in SEQ ID NO:2 or a variant thereof that encodes a bactericidal polypeptide.

According to a yet further aspect of the invention there is provided a polypeptide or nucleic acid encoding the said polypeptide as herein before described wherein the polypeptide has an inhibitory effect on biofilm formation by a biofilm-producing bacterium.

According to a yet further aspect of the invention there is provided a pharmaceutical composition comprising the polypeptides as herein before described.

According to a yet further aspect of the invention there is provided an item impregnated with or coated in or covered by the peptides of the present invention, the item being selected from the group comprising a medical device, medical instrument, medical implement, prosthetic, implantable device or material or tissue and wound dressing.

According to a yet further aspect of the invention there is provided a biologically compatible material selected from the group comprising cement, glue, composite, tissue matrix or scaffold or wound dressing incorporating or impregnated with the peptides of the present invention.

According to a yet further aspect of the invention there is provided a dental preparation comprising the polypeptides as herein before described.

BRIEF DESCRIPTION OF THE DRAWINGS

Embodiments of the invention are further described hereinafter with reference to the accompanying drawings, in which:

FIG. 3 shows the DNA sequence of 156 bp [SEQ ID NO:2] containing the structural gene of peptide NI01 and the deduced amino acid sequence [SEQ ID NO:3].

FIG. 4 shows the alignment of peptide NI01 [SEQ ID NO:3 as single letter code] and related peptides lacticinZ [SEQ ID NO:4] and LactocinQ [SEQ ID NO:5] as identified by BLAST protein search, identical residues are highlighted by asterisks.

FIG. 5 shows the effect of peptide NI01 on *Staphylococcus epidermidis* strain 156.

DETAILED DESCRIPTION

Figure 1:
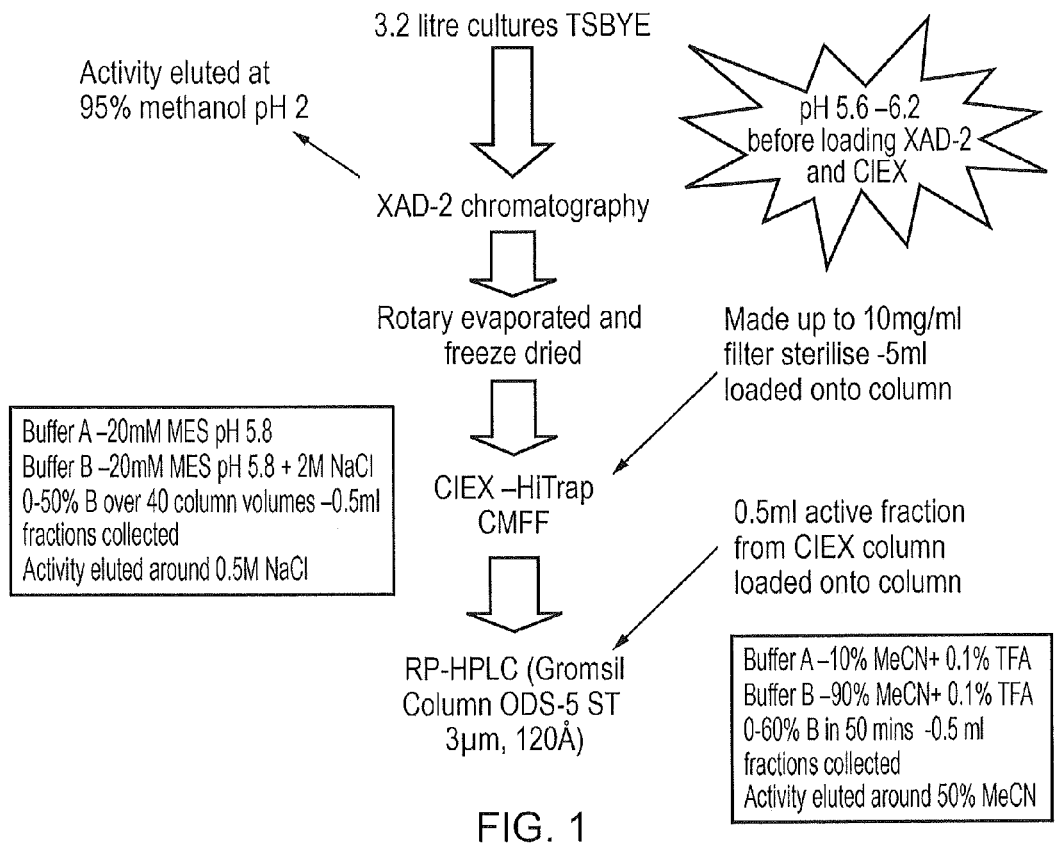
FIG. 1 shows a schematic diagram of methods used to purify peptide NI01 from culture medium enabling identification.

The terms "polypeptide," "peptide," and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins.

A "variant" polypeptide comprises a polypeptide sequence that differs in one or more amino acid residues from the polypeptide sequence of a parent or reference polypeptide (such as, e.g., a wild-type (WT) polypeptide sequence). In one aspect, a variant polypeptide comprises a polypeptide sequence which differs from the polypeptide sequence of a parent or reference polypeptide in from about 1%, 2%, 3%, 4%, 5%, 6%, 7%, 8%, 9%, 10%, 11%, 12%, 13%, 14%, 15%, 20%, 30% 40%, 50% or more of the total number of residues of the parent or reference polypeptide sequence. In another aspect, a variant polypeptide comprises a polypeptide sequence that has at least about 50%, 60%, 70%, 80%, 85%, 86%, 87%, 88%, 89%, 90%, 91%, 92%, 93%, 94%, 95%, 96%, 97%, 98%, or 99% sequence identity to the polypeptide sequence of a parent or reference polypeptide. In another aspect, a variant polypeptide comprises a polypeptide sequence that differs from the polypeptide sequence of a parent or reference polypeptide in from 1 to 100 or more amino acid residues (e.g., 1, 2, 3, 4, 5, 6, 7, 8, 9, 10, 11, 12, 13, 14, 15, 16, 17, 18, 19, 20 or more amino acid residues). A variant polypeptide may comprise a polypeptide sequence that differs from the polypeptide sequence of a parent or reference polypeptide by, e.g., the deletion, addition, or substitution of one or more amino acid residues (e.g., 1, 2, 3, 4, 5, 6, 7, 8, 9, 10, 11, 12, 13, 14, 15, 16, 17, 18, 19, 20 or more amino acid residues) of the parent or reference polypeptide, or any combination of such deletion(s), addition(s), and/or substitution(s). The reference or parent polypeptide may itself be a variant polypeptide.

A nucleic acid or polypeptide is "recombinant" when it is artificial or engineered, or derived from an artificial or engineered protein or nucleic acid.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Certain variant proteins encompassed by the present invention are biologically active, that is, they continue to possess the desired biological activity i.e. bacteriocidal, as described herein. Biologically active variants of the polypeptides of the present invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequences as determined by sequence alignment programs and parameters The invention features polypeptides, preferably substantially pure preparations of polypeptides, or recombinant polypeptides. In preferred embodiments: the polypeptide has biological activity; the polypeptide has an amino acid sequence at least 55%, 60%, 70%, 80%, 90%, 95%, 98%, or 99% identical to an amino acid sequence of the invention as depicted in either SEQ ID NO:1 or 3, preferably it has about 65% sequence identity with an amino acid sequence of the, and most preferably it has about 90% to about 99% sequence identity with an amino acid sequence of the invention. The polypeptide is at least 10, 14, 20, 25, 30, 35, 40 45 or 50 amino acid residues in length; the polypeptide includes at least 10 and more preferably at least 14 or more contiguous amino acid residues of the invention contained in the Sequence Listing.

The peptides of the present invention are bactericidal that is to say they are capable of preventing infection by inhibiting the growth or action of microorganisms by for example killing or destroying bacteria and/or or they may have an inhibitory effect on biofilm formation by a biofilm-producing bacterium.

A "biofilm" is a complex organization of bacteria that are anchored to a surface via a bacterially extruded exopolymeric matrix, and grow into differentiated micro-colonies. The extruded exopolymeric matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because of a lack of accessibility by immunoglobulin and complement. The attachment of bacteria to a surface triggers the expression of a cassette of genes, which results in the formation of a biofilm. A "biofilm phenotype" confers to a bacterium possessing a reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces.

Preferably the peptides of the present invention are "inhibitory" that is to say they prevent or reduce the bacteria's ability to form biofilms. Preferably the bacterial infections that can be treated by the peptides of the present invention are selected from the group comprising *Staphylococcus, Streptococcus, Enterococcus* (including Vancomycin-resistant *Enterococcus faecalis:* VRE), *Bacillus* and *Listeria*.

Preferably, the bacterial infection is as a result of an infection caused by, but not limited to, the following bacteria selected from the group comprising *Staphyloccus saprophyticus, Staphyloccocus xylosus, Staphyloccocus lugdunensis, Staphyloccocus schleiferi,*

*Stapylococcus caprae ,Staphylococcus epidermidis, Staphylococcus hominis, Staphylococcus saprophyticus, Staphylococcus warneri, Staphylococcus aureus*, MRSA, *Enterococcus faecalis* (including Vancomycin-resistant *enterococcus* VRE), *Proprionibacterium acnes, Bacillus cereus, Bacillus subtilis, Listeria monocytogenes, Streptococcus pyrogenes, Streptococcus salivarius, Streptococcus mutans* or *Streptococcus pneumoniae* and more preferably is as a result of a Staphylococcal infection and more preferably still is a *S. epidermidis* infection.

The present invention also provides a method of killing or damaging bacteria. The method involves contacting the bacteria with the antimicrobial peptides of the invention. In some instances, the bacteria will be killed outright, and signs or symptoms of bacterial colonization or infection will be completely eradicated. However, those of skill in the art will recognize that much benefit can be derived even if all bacteria in a population are not killed outright. For example, in some cases, the ability of the bacteria to carry out metabolic reactions may be slowed or otherwise attenuated by exposure to the antimicrobial peptides, or the reproductive potential of the bacteria may be decreased. All such lessening of the bacteria's ability to flourish in an environment in which they would typically establish colonies and biofilms and persist may be of benefit to a host organism in need of treatment with the antimicrobial peptides of the invention.

While in one embodiment of the invention, treatment of bacterial host organisms or potential bacterial host organisms is contemplated (e.g. humans and other mammals, so that veterinary uses are also included), other uses of the antimicrobial peptides of the invention will also occur to those of skill in the art. For example and without limitation, the treatment of surfaces of synthetic or natural implants, prosthetics, surgical instruments and implements. Preferably, the invention includes impregnating or coating or covering items such as, without limitation, surgical gloves, catheters, artificial joints, breast implants, heart valves, pace makers and so on in the peptides of the present invention. In another embodiment of the invention it is envisaged that the peptides of the present invention may be included in a cement or glue or wound dressing or matrix. These particular embodiments are particularly advantageous as the only truly effective way of treating an individual with an implanted medical device that is infected with *S. epidermidis* is in its removal. Thus it will be appreciated that the present invention, which can mitigate such infections, would offer immediate benefit to patients and clinicians alike and also have an impact on reducing hospital costs.

Preferably, the peptides of the present invention are used to coat or cover or at least provide an overlayer for plastics items, for example and without limitation a polyethylene surface. In addition to providing a coating or covering metal surfaces.

In a further embodiment of the invention the peptides of the present invention can included in a dental preparation. Preferably, the dental preparation is selected from the group comprising a gel, spray, mouthwash, toothpaste, lozenge or chewing gum. It will be appreciated that a dental preparation containing the peptides of the present invention will be of particular utility in reducing the number of *Streptococcus mutans* which are important causes of dental caries.

Accordingly in one aspect of the invention the polypeptides of the present invention are for use in the treatment of dental and gum diseases.

It will be appreciated that the present invention provides novel peptides and in particular a peptide designated as peptide NI01 that is obtained from a Staphylococcal culture. Results described hereinafter show that peptide NI01 is rich in tryptophan and lysine but it does not contain cysteine or the pediocin box typical to class II bacteriocins and that it is highly cationic compared to most closely related peptides. Peptides rich in lysine have been found to retain potent antimicrobial activity, but have reduced haemotoxicity and cytotoxicity. Peptide NI01 is also highly heat and pH stable. Peptide NI01 shows a maximum of 51% identity to any other known peptides, its N-terminal sequence is similar to lacticin Q and Z (bacteriocin derived from corn) up to residue 37 thereafter the C terminal appears to be unique as it only shares a conserved tryptophan at position 41, isoleucine at position 46 and leucine at position 47.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLE 1

As described in FIG. 1, a combination of XAD-2, a poly di-vinyl benzene hydrophobic resin was employed to initially capture the peptide from the growth media. The active fractions eluted from this step were then applied to a cation exchange column (CIEX), separating the peptide based on its charge, this was used as an intermediate purification step prior to HPLC. RP-HPLC was used as the final purification step to achieve the pure peptide. MALDI analysis of NI01 RP-HPLC active fraction revealed a mass of 6074.842 for the peptide.

Purified HPLC fractions containing peptide NI01 were analysed using mass spectrometry following a trypsin digest. This enabled the partial sequence of peptide NI01 to be obtained: I/LNAGQSFEWI/LYK (1640.8 Da) see SEQ ID NO:2. The entire genome of producer NI01 was sequenced using pyrosequencing and the genome data was then interrogated with the sequences above obtained using the mass spectrometer. The sequence NAGQSFEW [SEQ ID NO:5] located the structural gene of the peptide within producer NI01.

FIG. 3 shows the DNA sequence of 156bp [SEQ ID NO:2] containing the structural gene of peptide NI01, the deduced amino acid sequence is shown above the DNA sequence [SEQ ID NO:2]. FIG. 4 shows the alignment of peptide NI01 [SEQ ID NO:3 as single letter code] and related peptides as identified by BLAST protein search, identical residues are highlighted by asterisks. In BLAST search of the amino acid and nucleotide sequences of peptide NI01 showed 51% identity to lacticinZ [SEQ ID NO:4], 48% identity to LactocinQ [SEQ ID NO:5] and 38% identity Aureocin A53 (not shown). This data confirms that peptide NI01 of the present invention is novel. The N-terminal sequence NI01 and lacticin Q and Z are quite similar up to residue 37. The C terminal sequence QSFEWIYKQIKKLWA [SEQ ID NO:1] only shares a conserved tryptophan at position 41, Isoleucine at position 46 and leucine at position 47, thus these residues could be essential for the activity or specificity of the peptide.

EXAMPLE 2

The inhibitory activity of peptide NI01 against infective Staphylococcal strains was assessed. Sixty Staphylococcal isolates associated with joint or tissue infections were obtained and the inhibitory effect of peptide NI01 on a score of 1-3 was gauged. The scoring system used for the deferred antagonism method is shown in FIG. 1, NI indicates no inhibition. FIG. 5 shows the inhibitory effect over a 100 hour period of peptide NI01 on isolate *Staphylococcus epidermis* 156 which is a biofilm forming strain isolated from infected acetabulum tissue, the score is +3.

Results are summarised in Table 1 and show that peptide NI01 inhibited 58 out of the 60 (91%) clinical biofilm forming isolates of *Staphylococci* associated with joint and/or tissue infections many of which are resistant to traditional prior art antibiotic therapies such as gentamicin and methicillin, thus showing its utility against a vast range of different Staphylococcal infections and ones known to have resistance to prior art therapies.

Figure 2:
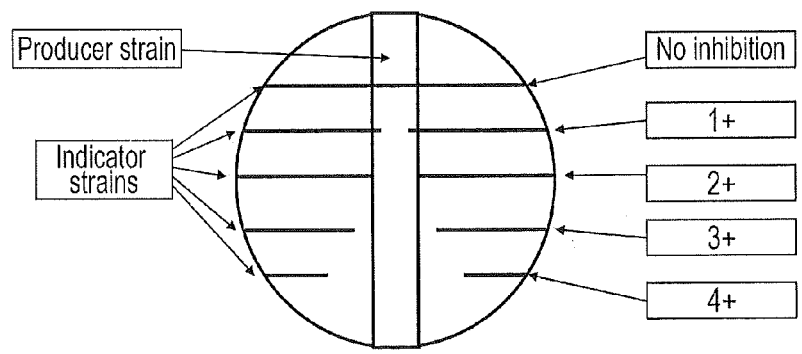
FIG. 2 shows the scoring system used for the deferred antagonism method.

Table 2 shows the minimum inhibitory concentration (MIC in µg/ml) of peptide NI01 against a range of clinically relevant bacteria. Data were obtained using published micro-dilution methods, as recommended by the British Society for Antimicrobial Chemotherapy. Purified preparations of NI01 have also been seen to have activity against *Propionibacterium acnes* using a spot on lawn method. In addition, activity of the parent strain has been tested using the deferred antagonism assay, indicating the ability to inhibit growth of the following bacteria (scoring as described in FIG. 2): *Staphylococcus xylosus* (2+), *Streptococcus pyogenes* (2+), *Streptococcus pneumoniae* (3+), and *Streptococcus salivarius* (1+).

The inhibitory activities observed indicate that NI01 could be used in the prevention or treatment of infections not limited to the following: skin and soft tissue infections caused by *Enterococci, Proprionibacterium* acnes, *Staphylococci* or *Streptococci*; bacterial food poisoning caused by *Staphylococci, Bacillus* or *Listeria*; and medical device related infections caused by *Enterococci, Staphylococci* or *Streptococci*.

The MIC values indicate that NI01 has potent activity against *Streptococcus mutans* and that eradication of these organisms from the tooth surface may contribute to a reduced level of dental caries. The peptide NI01 is therefore an ideal candidate additive in for example, toothpaste, to reduce the number of *Streptococci mutans*.

EXAMPLE 3

In tests to assess enzyme stability of peptide NI01 and to further characterise the peptide, treatment of partially purified peptide NI01 with RNase, DNase, lysozyme, lipase and α-amylase caused no effect on activity compared to the control of the peptide in molecular water. Following treatment with protease a 75% reduction was observed in activity from 640 AU/ml to 160 AU/ml, the same result was observed following treatment with proteinase K. The arbitrary unit (AU) was defined as the reciprocal of the highest dilution producing a clear zone of growth inhibition of the indicator strain. Treatment with trypsin resulted in a 50% reduction of activity from 640 AU/ml to 320 AU/ml. These results provide evidence for the proteinacous nature of peptide NI01. The peptide was not affected by a amylase or lipase, indicating it does not contain polysaccharide or lipid moieties.

EXAMPLE 4

Figure 6:
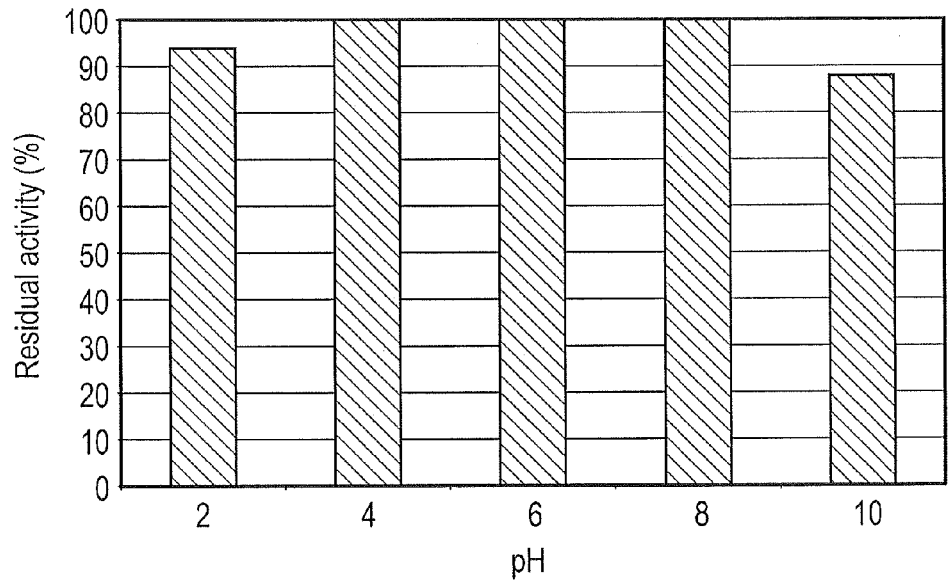
FIG. 6 shows the pH stability of peptide NI01.
Figure 7:
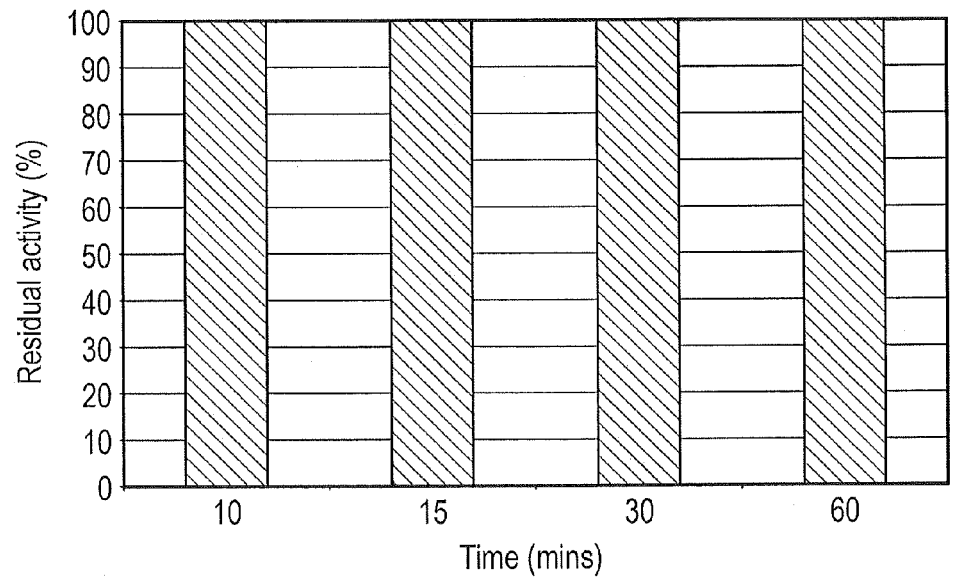
FIG. 7 shows the heat stability of peptide NI01.

Further tests were conducted to assess the growth characteristics, pH and heat stability of peptide NI01. Growth studies identified that peptide NI01 is produced in late log to early stationary phase at around 7.5 hours which is characteristic of bacteriocins. FIG. 6 shows the relative activity of the peptide over a wide range (2-10) of pH values 2. 100% activity was retained between pH 4-8 whilst only about 5% was lost at acidic pH 2 and 12% lost at alkaline pH 10. Turning to FIG. 7 peptide NI01 showed extreme heat stability as it retained 100% activity following exposure to 80° C. for 10, 15, 30 and 60 minutes. These studies confirm the stability of peptide NI01 under a variety of adverse conditions.

EXAMPLE 5

Figure 8:
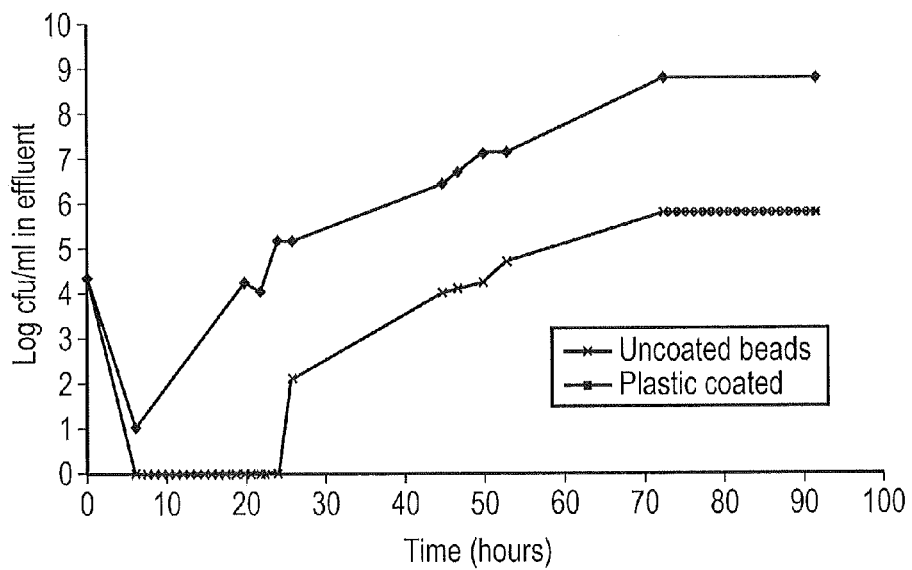
FIG. 8 shows the effect of coating polyethylene in peptide NI01 on strain 156 biofilm formation.
Figure 9:
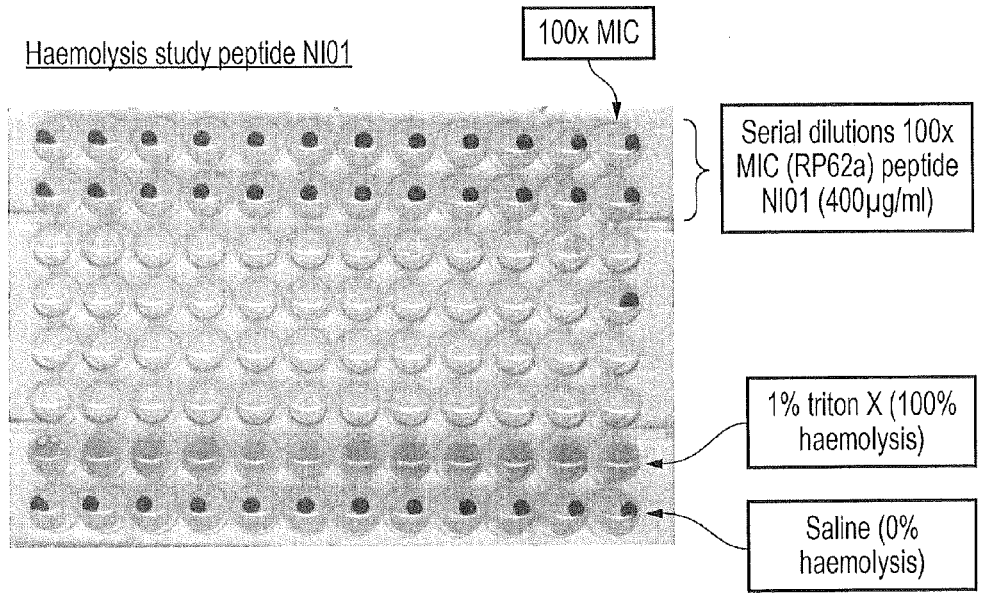
FIG. 9 shows a haemolysis assay of peptide NI01.

4 mm diameter polyethylene beads were submerged in a semi-pure preparation of peptide NI01 for 2 hours. The beads were then left to dry for 1 hour before incorporation into a model analysis system. 10 beads were used per housing unit for both the coated and uncoated beads. Each of the 10 beads were inoculated with a standard inoculums ($3 \times 10^8$ cfu/ml) of strain 156 as hereinbefore described. Each experiment was carried out in triplicate. Paired t tests were conducted to determine the statistical significance of results using SPSS v15 software. Results showed a reduction of 2.85 log units (p=0.000) and that peptide NI01 adhered to polyethylene surface (FIG. 8). Standard haemolysis studies were conducted using >10× minimum inhibitory concentration (MIC) stock peptides. The results showed that peptide NI01 is not haemolytic at 100× MIC (FIG. 9) thus indicating its safety as a therapeutic. These studies show that peptide NI01 can be successfully coated onto polyethylene surfaces and that it does not induce haemolysis making it an ideal candidate for coating or impregnating prosthetic implants and the like.

EXAMPLE 6

Figure 10:
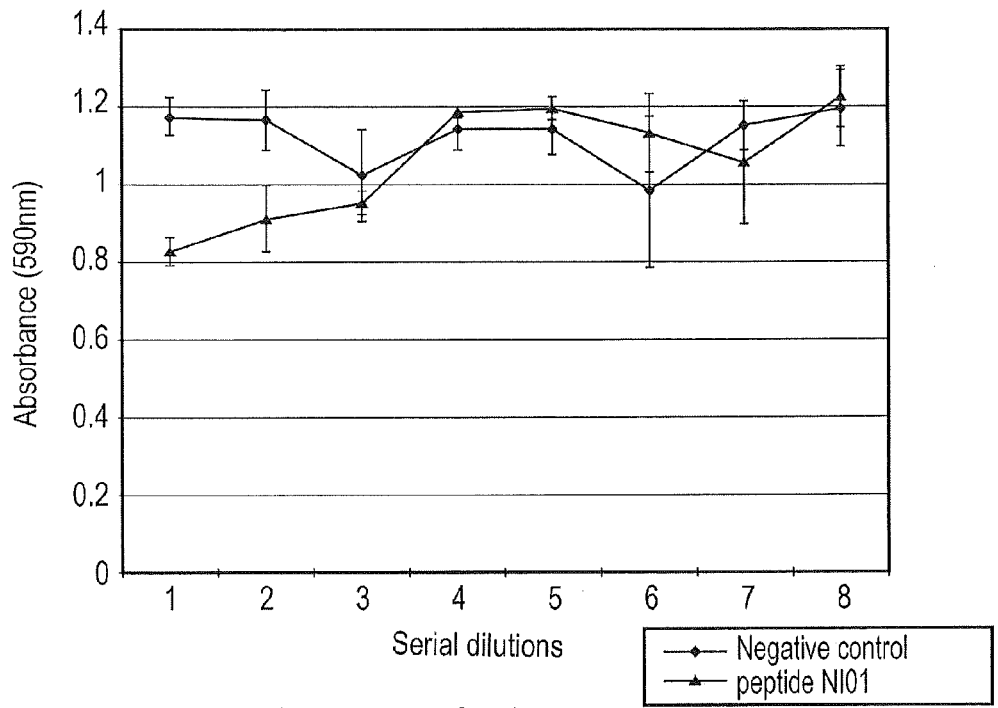
FIG. 10 shows the effect of peptide NI01 on vero cell line.

Studies to visually observe the effects on vero cells following incubation with peptide NI01 using light microscope were undertaken. Following incubation of the peptide with vero cells for 24 hours at 25× MIC dilution, about 10-20% of the cells looked apoptotic but cells incubated with 12.5× were healthy with no signs of damage. Following 48 hours incubation with the peptide cells appeared healthier and were actively replicating. FIG. 10 shows the effect of peptide NI01 on vero cell line. Serial dilutions of peptide NI01, suspended in phosphate buffered saline (PBS), were applied to vero cells, with the highest concentration of peptide being 25× MIC. A negative control of PBS was used. No significant damage to the vero cells was observed even at the highest concentration of 25× MIC of peptide NI01 indicating the lack of toxic activity against animal cell lines.

The cytotoxic potential of peptide NI01 was investigated by exposing primary human dermal fibroblast cultures to a range of test concentrations between 1 µg/ml and 400 µg/ml for 24 hours. Two endpoints were measured using standard methods: metabolic activity (indicated by reduction of the tetrazolium salt MTT); and membrane integrity (indicated by neutral red uptake, NRU). The data indicate that peptide NI01 did not cause significant cytotoxicity at any concentration tested (ie at 400 µg/ml or lower), in terms of metabolic activity or membrane damage.

EXAMPLE 7

Spontaneous mutation rates and passaging experiments were conducted. Results were obtained from the single-step mutation tests at two, four and eight times the MIC of peptide NI01 against reference strain RP62a, gentamicin resistant clinical isolate 53 and gentamicin sensitive isolate 156. No evidence of mutation was observed with these three strains against peptide NI01 ($<1.5 \times 10^8$ cfu/ml). Twelve clinical biofilm forming strains of CNS staphylococci species associated with prosthetic joint infections were passaged in sub-inhibitory concentrations. Only two strains showed a two fold increase in the MIC of peptide NI01. Strain 12, a gentamicin resistant clinical isolate showed an increase in MIC from 3.9 mg/ml to 7.8 mg/ml. Strain 11, a gentamicin and methicillin resistant clinical isolate showed an increase in MIC from 7.8 mg/ml to 15.6 mg/ml. All of the other strains tested exhibited no change in MIC values. These experiments indicate the limited ability of CNS strains to develop resistance to the activity of peptide NI01 under laboratory conditions

EXAMPLE 8

Figure 11:
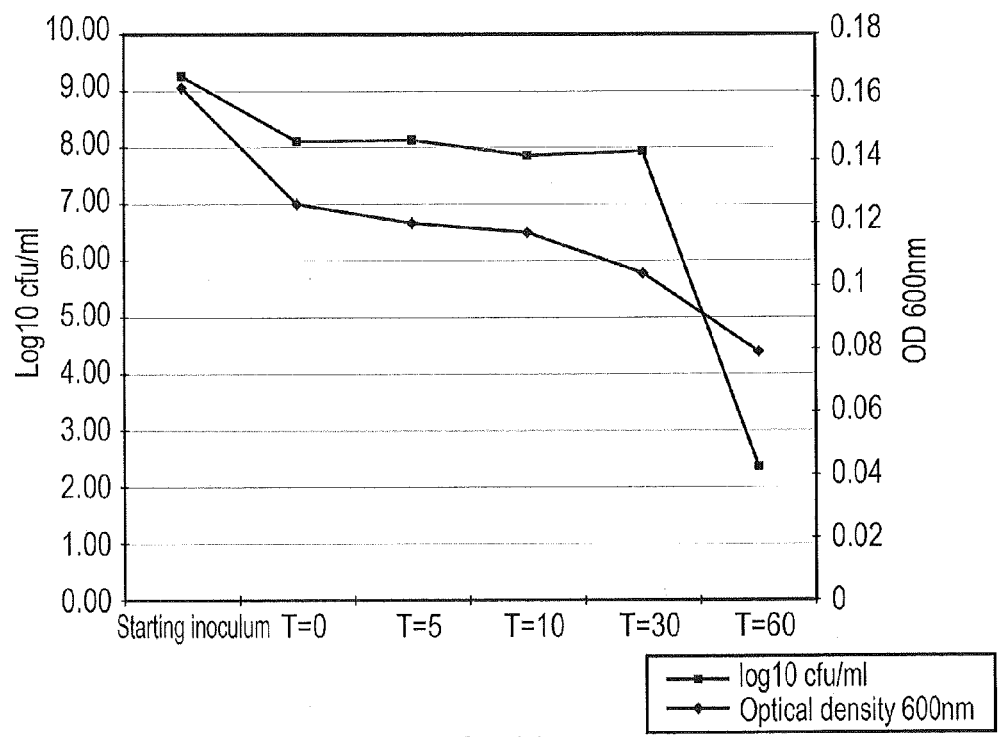
FIG. 11 shows the effect of peptide NI01 on the viability and optical density of indicator strain *S. epidermidis* 156.

Assessment of the bacterial killing mechanisms of peptide NI01 gram staining was also carried out on the cells at varying time points following addition of the peptides. FIG. 11 shows the effect of peptide NI01 on the viability and optical density of indicator strain *S. epidermidis* 156. Following addition of peptide NI01 to *S. epidermidis* strain 156 at T=30, there was a rapid decrease in the cfu count, that was not as pronounced in the optical density readings. This indicates a bactericidal, but non-lytic activity against the target bacterium confirming the mode of action of NI01 as a membrane destabilizing, non-lytic agent. When treated cells were examined using microscopy (Gram stain), there were dramatic changes in the cell staining indicating a define effect on the membrane. Prior to addition of peptide at least 150 small cocci were observed per field of view but following addition of peptide the number of stained cells dramatically decreased to less than 20 cells per field of view indicating that the cells were no longer able to take up the stain. Results therefore indicate the peptide induces membrane damage and disruption in this organism.

Figure 12:
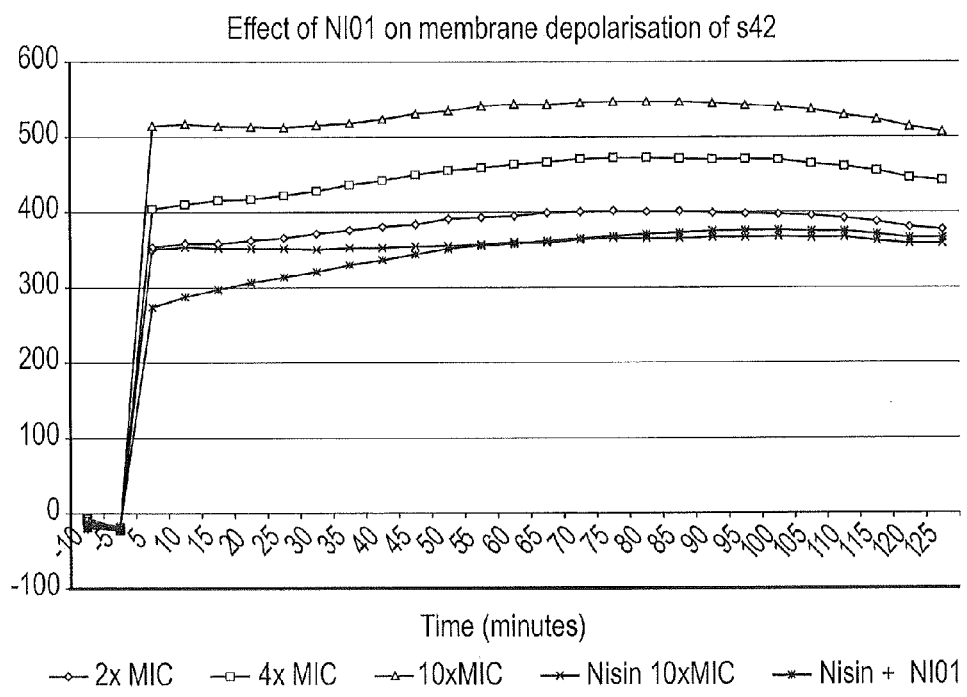
FIG. 12 shows the effect of NI01 on the membrane potential of *S. epidermidis* s42 at a range of concentrations.
Figure 13:
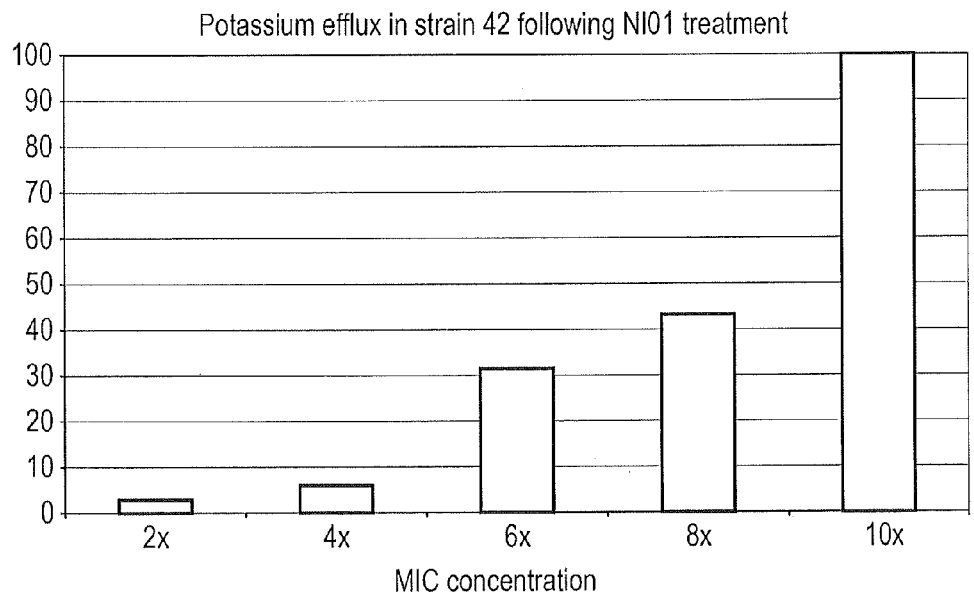
FIG. 13 shows potassium release from indicator strain *S. epidermidis* s42 monitored using the K+ sensitive fluorescent dye PBFI.
Figure 14:
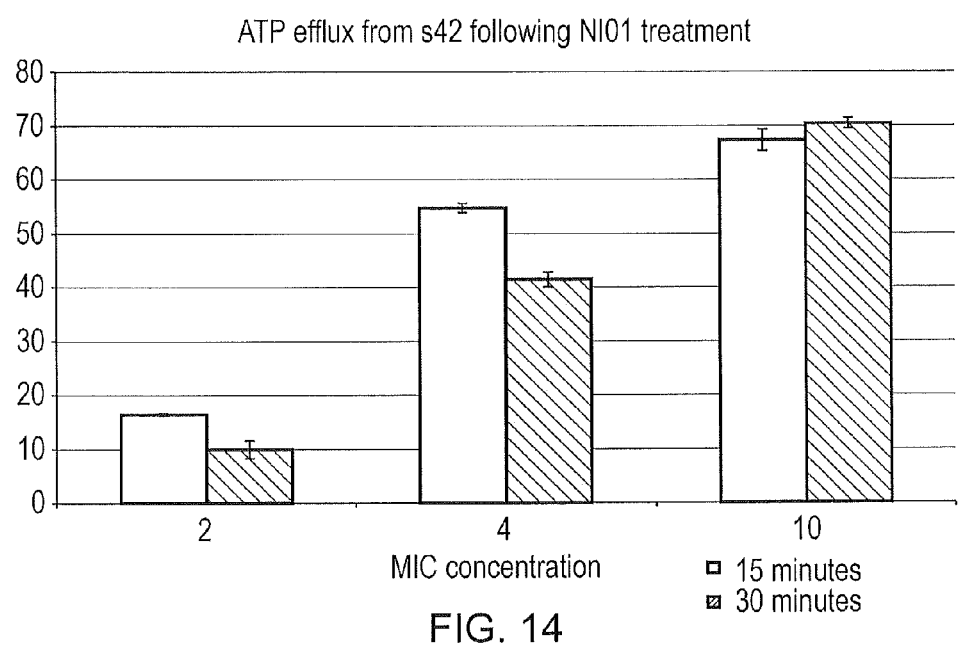
FIG. 14 shows ATP released from indicator strain *S. epidermidis* s42 following exposure to NI01 at various time points.

FIG. 12 shows the effect of NI01 on the membrane potential of *S. epidermidis* s42 at a range of concentrations and that NI01 rapidly depolarized the membrane at all concentrations assessed, and that the levels achieved exceeded that obtained for the positive control (nisin 10× MIC). FIG. 13 shows potassium release from indicator strain *S. epidermidis* s42 monitored using the K+ sensitive fluorescent dye PBFI. Results are expressed as % of positive control and that NI01 causes concentration dependent release of potassium from indicator cells with 100% being released at the highest concentration of NI01 assessed (10× MIC). FIG. 14 shows ATP released from indicator strain *S. epidermidis* s42 following exposure to NI01 at various time points. Results are expressed as % of positive control and show that NI01 causes ATP efflux from indicator *S. epidermidis* s42 in a concentration dependent manner, with the highest amount of ATP released (>65%) at 10× MIC.

In summary, mode of action studies, using DiSC3(5) [3,3'-Dipropylthiadicarbocyanine iodide] assays, indicate that NI01 depolarises the membrane (FIG. 12) of the a *Staphylococcus epidermidis* strain resulting in loss of potassium (FIG. 13) and ATP (FIG. 14).

EXAMPLE 9

Figure 15:
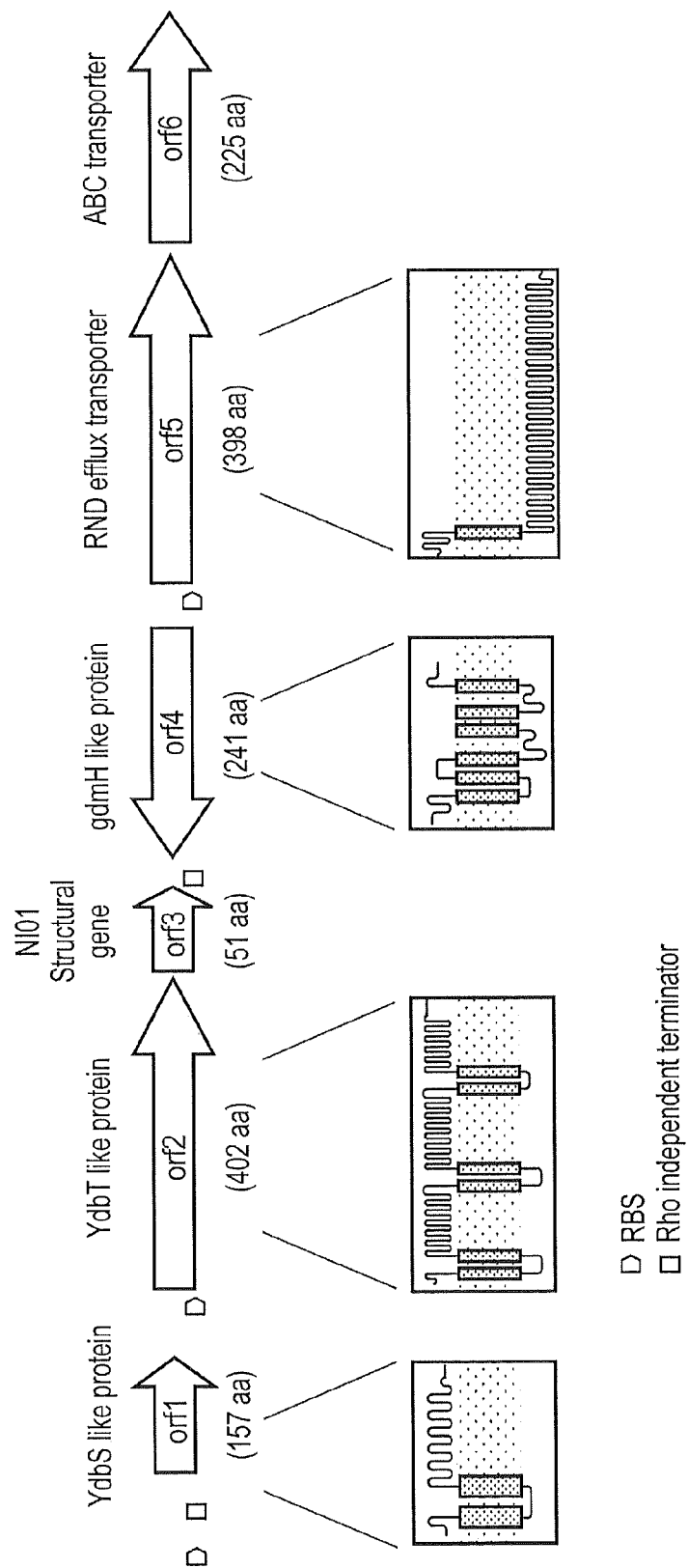
FIG. 15 shows the genomic environment of the peptide NI01 structural gene and related genes.

Table 3 and FIG. 15 show genes neighboring the peptide NI01 structural gene. This information demonstrates the fact that peptide NI01 is encoded by a genetic locus that has similarity (in organization and, to an extent, content) to previously described bacteriocin loci, which supports the suggestion that the genes identified in strain NI01 are responsible for production of an active peptide.

Figure 16:
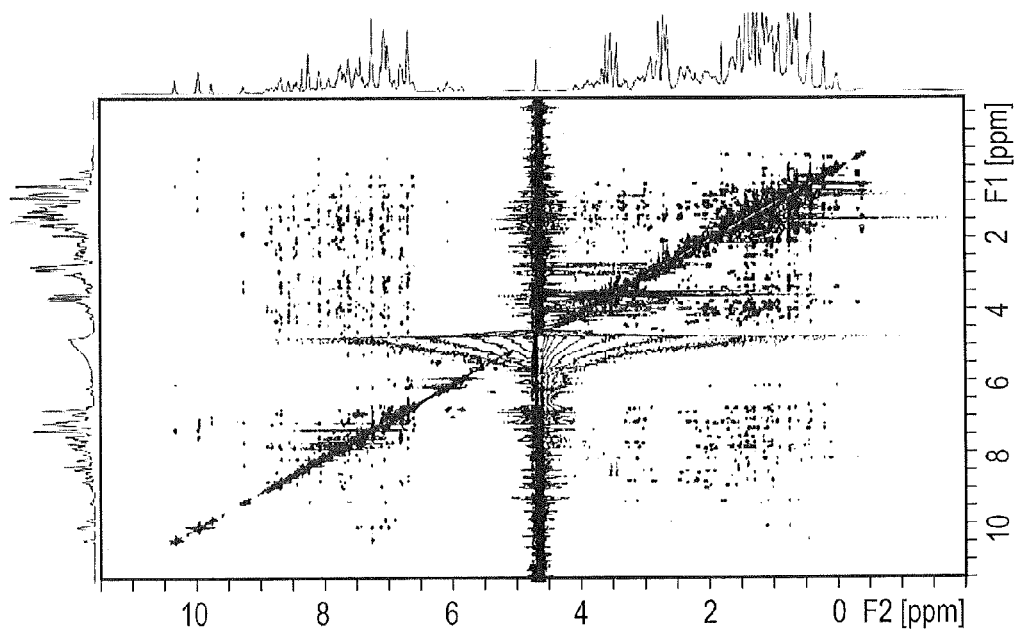
FIG. 16 shows the 20 1 H/1 H NOESY spectrum of NI01.

Preliminary NMR $^1$H/$^1$H spectra show excellent signal dispersion and line widths consistent with formation of a monomer (FIG. 16). Combined with in silico prediction, these analyses provide evidence that NI01 forms a globular helical structure.

TABLE 1

| Sample number | Specimen type | Antibiotic resistance | Inhibition caused by NI01 |
| --- | --- | --- | --- |
| S1 | Tissue | meth, pen, ery, amp, flu, gen, trim, cip | 2+ |
| S2 | Joint fluid | pen, ery, amp, flu, gen, trim, cip | 2+ |
| S4 | Tissue | meth, flu, gen, trim | 3+ |
| S5 | Tissue | met | 3+ |
| S6 | Femoral canal | flu, ery, gen, rif, cip | 1+ |
| S7 | Femoral canal | sensitive | 1+ |
| S8 | Tissue | flu, ery, gen, rif, cip | 1+ |
| S9 | Tissue | flu, ery, gen, rif, cip | 3+ |
| S10 | Tissue | flu, ery, gen, rif, cip | 1+ |
| S11 | Tissue | flu, ery, gen, rif, cip | 2+ |
| S12 | Tissue | flu, ery, rif, cip | 1+ |
| S13 | Swab | flu, ery, gen, rif, cip | 1+ |
| S25 | Swab (left hip joint) | meth, gen | 2+ |
| S28 | Tissue (femoral canal) | meth, gen | 3+ |
| S30 | Tissue (left capsule) | meth | 3+ |
| S31 | Swab (joint) | sensitive | 2+ |
| S37 | Tissue (knee) | sensitive | 2+ |
| S39 | Tissue (right knee) | meth, flu, fus, cip | 1+ |
| S40 | Tissue (right knee) | meth, flu, ery, fus, clin, cip | 1+ |
| S41 | Tissue (femoral canal) | meth, flu, fus, cip | 1+ |
| S42 | Tissue (right knee) | meth, flu, fus, cip | NI |
| S43 | Swab (right hip joint) | meth, flu, ery, fus, clin, cip | NI |
| S44 | Swab (right hip joint) | meth, flu, ery | NI |
| S46 | Swab (right hip joint) | meth, flu, gen, fus, cip | NI |
| S47 | Swab (tibia) | meth, flu, ery, gen, fus, cip | NI |
| S48 | Tissue (left knee) | meth, flu, ery, gen, fus, cip | 1+ |
| S49 | Tissue (left knee) | meth, flu, ery, gen, fus, cip | 2+ |
| S52 | Tissue (right hip joint) | gen, cip | 2+ |
| S53 | Swab (femur) | gen, cip, fus | 2+ |
| S56 | Tissue (right hip joint) | sensitive | 2+ |

TABLE 1-continued

| Sample number | Specimen type | Antibiotic resistance | Inhibition caused by NI01 |
| --- | --- | --- | --- |
| S60 | Tissue (femur) | gen, trim | NI |
| S71 | Swab (femur) | flu | 2+ |
| S78 | Tissue (right elbow) | flu, ery | 1+ |
| S79 | Pus (right elbow) | meth, flu, ery | 1+ |
| S80 | Tissue (triceps) | flu, ery | 1+ |
| S81 | Pus (right elbow) | flu, ery | 1+ |
| S82 | Tissue (right elbow) | flu, ery | 1+ |
| S83 | Tissue (next to bone) | flu, ery | 1+ |
| S85 | Tissue (left elbow) | meth, ery | 1+ |
| S86 | Swab (right elbow) | sensitive | 2+ |
| S88 | Swab (left hip) | sensitive | 1+ |
| S89 | Tissue (right elbow) | meth, flu, ery | 1+ |
| S90 | Ulcer | flu, ery | 2+ |
| S91 | Swab (right acetabulum) | flu | 2+ |
| S92 | Swab (femur) | flu | 1+ |
| S93 | Tissue (wound) | flu, ery, gen, fus | NI |
| S94 | Tissue (right femur) | flu | 3+ |
| S95 | Tissue (right femur) | flu, trim | 3+ |
| S96 | Tissue (right femur) | flu | 1+ |
| S97 | Tissue (acetabulum) | flu | 3+ |
| S106 | Neck of femur | ery, fus | 3+ |
| S127 | Tissue (screw holes) | flu | 1+ |
| S128 | Tissue (under plate) | meth, flu | 1+ |
| S133 | Tissue (acetabulum) | flu | 2+ |
| S156 | Tissue (acetabulum) | ery, fus | 3+ |
| S159 | Swab (right thigh) | meth, flu, ery | 1+ |
| S160 | Swab (right hip) | meth, flu, gen | 2+ |
| S161 | Swab (right hip sinus) | flu, ery, gen, fus, cip | 2+ |
| S163 | Tissue (right hip) | flu, ery, gen, fus, cip | 1+ |
| S164 | Tissue (right hip) | ery, fus, amp, clin | NI |

TABLE 2

| Strain | MIC pg/ml |
| --- | --- |
| *S. epidermidis* s1 | 1 |
| *S. epidermidis* s2 | 4 |
| *S. epidermidis* s37 | 2 |
| *S. epidermidis* s42 | 2 |
| *S. epidermidis* s44 | 4 |
| *S. epidermidis* s60 | 2 |
| *S. epidermidis* s93 | 2 |
| *S. epidermidis* s156 | 0.0625 |
| *S. epidermidis* RP62a | 2-4 |
| *S. saprophyticus* | 0.5-1 |
| *S. hominis* | 1 |
| *S. warneri* | 1 |
| MRSA s37 (EMRSA 15) | 1-2 |
| MRSA s41 (EMRSA 15) | 1-2 |
| MRSA s71 (EMRSA 15) | 2 |
| *S. aureus* 1195 | 2 |
| *Enterococcus faecalis* | 1 |
| Vancomycin resistant *Enterococcus faecalis* 1 | 1 |
| Vancomycin resistant *Enterococcus faecalis* 2 | 1 |
| Vancomycin resistant *Enterococcus faecalis* 3 | 1 |
| Vancomycin resistant *Enterococcus faecalis* 4 | 1-2 |
| Vancomycin resistant *Enterococcus faecalis* 5 | 0.5-1 |
| Vancomycin resistant *Enterococcus faecalis* 6 | 0.5 |
| *Streptococcus mutans* 263 | 2 |
| *Streptococcus mutans* 313 | 0.12 |
| *Bacillus cereus* | <0.125 |
| *Bacillus subtillis* | <0.125 |
| *Listeria monocytogenes* | <0.125 |

TABLE 3

| Open reading frame (orf) | Co-ordinates | Function |
| --- | --- | --- |
| Orf1 | 20562-20735 | No significant similarity |
| Orf2 | 20570-20917 | Hypothetical protein |
| Orf3 | 20975-21448 | 34% identity YdbS like protein |
| Orf4 | 21146-21322 | No significant similarity |

TABLE 3-continued

| Open reading frame (orf) | Co-ordinates | Function |
|---|---|---|
| Orf5 | 21347-21733 | Hypothetical proteins |
| Orf6 | 21444-22253 | 33% identity YdbT like protein |
| Orf7 | 22220-22861 | 31% identity YdbT like protein |
| Orf8 | 22884-23102 | Structural gene 51% identity to lacticin Z |
| Orf9 | 23149-23442 | Unknown protein |
| Orf10 | 23443-23751 | Hypothetical protein |
| Orf11 | 23805-24377 | Hypothetical protein |
| Orf12 | 24378-24533 | Hypothetical protein |

TABLE 3-continued

| Open reading frame (orf) | Co-ordinates | Function |
|---|---|---|
| Orf13 | 24403-25599 | 81% identity RND family efflux transporter |
| Orf14 | 24526-24738 | No significant similarity |
| Orf15 | 24530-24703 | No significant similarity |
| Orf16 | 25002-25166 | No significant similarity |
| Orf17 | 25151-25342 | No significant similarity |
| Orf18 | 25167-25463 | No significant similarity |
| Orf19 | 25604-26281 | 92% identity ATP transporter |

The invention claimed is:

1. An isolated or recombinant bactericidal polypeptide comprising a sequence of SEQ ID NO: 3 or variant thereof, said variant selected from the group consisting of:
    a) a polypeptide comprising a sequence having at least 90% sequence identity with SEQ ID NO: 3; and
    b) a polypeptide comprising one or more additional amino acid residues inserted into the amino acid sequence according to SEQ ID NO:3 and having at least 90% sequence identity with SEQ ID NO: 3,
    wherein the polypeptide is bactericidal.

2. An isolated or recombinant bactericidal polypeptide according to claim 1, wherein the polypeptide variant has at least, 90%, 95% or any integer up to 99% sequence identity with SEQ ID NO:3.

3. A method of treating a bacterial infection, wherein the method comprises administering an isolated or recombinant polypeptide according to claim 1, and the bacterial infection is selected from the group consisting of *Staphylococcus, Streptococcus, Enterococcus*, (including Vancomycin-resistant *Enterococcus faecalis*; VRE), *Bacillus* and *Listeria*.

4. A method of treating a bacterial infection according to claim 3, wherein the bacterial infection is caused by bacteria selected from the group consisting of *Staphyloccus saprophyticus, Staphyloccocus xylosus, Staphyloccocus lugdunensis, Staphyloccocus schleiferi, Staphylococcus caprae, Staphylococcus epidermidis, Staphylococcus saprophyticus, Staphylococcus warneri, Staphylococcus aureus, Staphylococcus hominis*, Methicillin-resistant *Staphylococcus aureus* (MRSA), *Enterococcus faecalis*, Vancomycin-resistant *Enterococcus* (VRE), *Proprionibacterium acnes, Bacillus cereus, Bacillus subtilis, Listeria monocytogenes, Streptococcus pyrogenes, Streptococcus salivariu, Streptococcus mutans* and *Streptococcus pneumoniae*.

5. The method of treating a bacterial infection according to claim 3, wherein the bacterial infection is a Staphylococcal infection.

6. The method of treating a bacterial infection according to claim 3, wherein the Staphylococcal infection is caused by a CNS species bacteria.

7. The method of treating a bacterial infection according to claim 3, wherein the infection is an *S. epidermidis* infection.

8. A pharmaceutical composition comprising the isolated or recombinant polypeptide of claims 1.

9. An item impregnated with, coated in or covered by the isolated or recombinant polypeptide according to claims 1, wherein the item is selected from the group consisting of a medical device, medical instrument, medical implement, prosthetic, implantable device or material or tissue, and wound dressing.

10. An item comprising a plastics or metal surface impregnated with, coated in or covered with the isolated or recombinant polypeptide according to claims 1.

11. A biologically compatible material selected from the group consisting of cement, glue, composite, tissue matrix, tissue scaffold and wound dressing incorporating or impregnated with the isolated or recombinant polypeptide according to claims 1.

12. A dental preparation comprising the isolated or recombinant polypeptide according to claims 1.

13. A dental preparation according to claim 12 selected from the group consisting of a spray, mouthwash, gel, paste, lozenge and chewing gum.

14. A method of treating a bacterial infection comprising administering a therapeutically effective amount of the pharmaceutical composition according to claim 8 to an individual in need of treatment.

15. The method according to claim 14, wherein the bacterial infection is caused by bacteria selected from the group consisting of *Staphyloccus saprophyticus, Staphyloccocus xylosus, Staphyloccocus lugdunensis, Staphyloccocus schleiferi, Staphylococcus caprae, Staphylococcus epidermidis, Staphylococcus saprophyticus, Staphylococcus warneri, Staphylococcus aureus, Staphylococcus hominis*, Methicillin-resistant *Staphylococcus aureus* (MRSA), *Enterococcus faecalis*, Vancomycin-resistant *Enterococcus* (VRE), *Proprionibacterium acnes, Bacillus cereus, Bacillus subtilis, Listeria monocytogenes, Streptococcus pyrogenes, Streptococcus salivariu, Streptococcus mutans* and *Streptococcus pneumoniae*.

16. The isolated or recombinant bactericidal polypeptide of claim 1, wherein the variant is a polypeptide comprising a sequence having at least 90% sequence identity with SEQ ID NO:3.

17. The isolated or recombinant bactericidal polypeptide of claim 1, wherein the variant comprises sequences representing marker moieties, tags or other functional polypeptide sequences.

* * * * *